United States Patent [19]

Curtis et al.

[11] Patent Number: 4,815,470
[45] Date of Patent: Mar. 28, 1989

[54] INFLATABLE SHEATH FOR ULTRASOUND PROBE

[75] Inventors: Bobby B. Curtis, Danville; Ivan A. Cermak, Santa Clara, both of Calif.

[73] Assignee: Advanced Diagnostic Medical Systems, Inc., Dublin, Calif.

[21] Appl. No.: 120,520

[22] Filed: Nov. 13, 1987

[51] Int. Cl.4 .............................................. A61B 10/00
[52] U.S. Cl. .............................................. 128/662.03
[58] Field of Search ............... 128/660, 661, 663, 244, 128/4; 374/209

[56] References Cited

U.S. PATENT DOCUMENTS

| 4,349,033 | 9/1982 | Eden | 128/660 |
| 4,593,699 | 6/1986 | Poncy et al. | 128/660 |
| 4,696,668 | 9/1987 | Wilcox | 128/24 A |

*Primary Examiner*—Francis J. Jaworski
*Assistant Examiner*—George Manuel
*Attorney, Agent, or Firm*—Sheldon R. Meyer

[57] ABSTRACT

Sheath 50, 100 for an ultrasound probe 52 includes a sheath body 70 and an end cap 76. The sheath body is disposed about the probe 52 with the end cap 76 disposed about the end 57 of the probe 52. A band 78 is disposed about the body 70 in order to define between the end cap 76 and the band 78 a portion of the sheath 50 which can be expanded with fluid pressure in order to properly position the probe in a human cavity. The end cap 76 prevents fluid from expanding the end of the sheath 50. Alternatively a toroidal chamber 118 can be defined by a first cylindrical body 102 of the sheath 100 in combination with a second cylindrical body 116. A conduit 120 is provided externally to the probe 52 and sheath 100 for introducing fluid into the toroidal chamber 118.

20 Claims, 4 Drawing Sheets

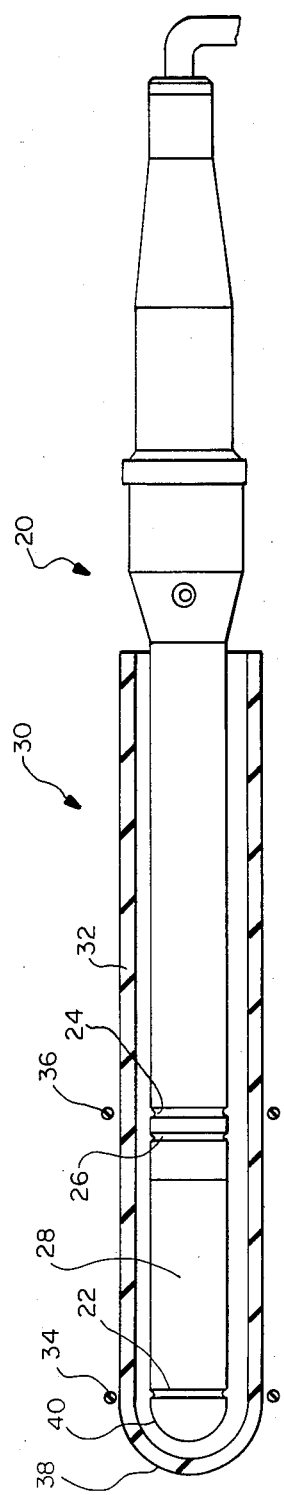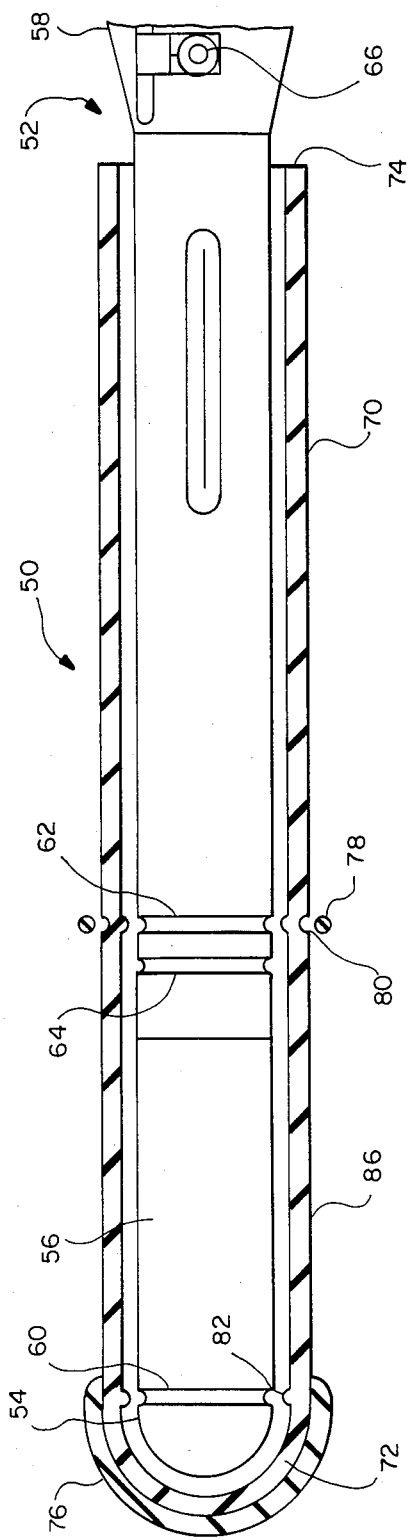

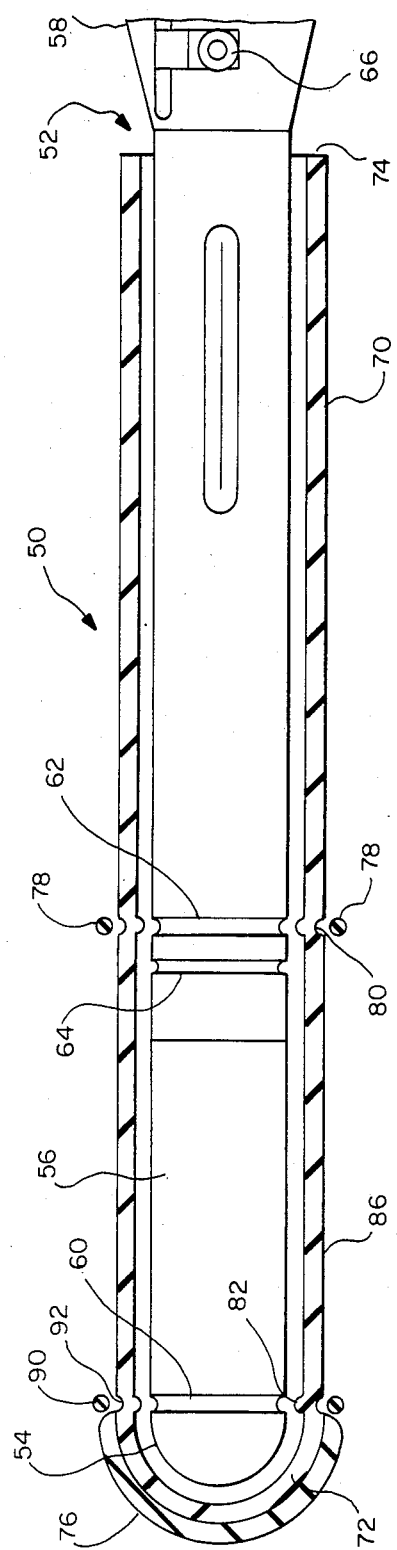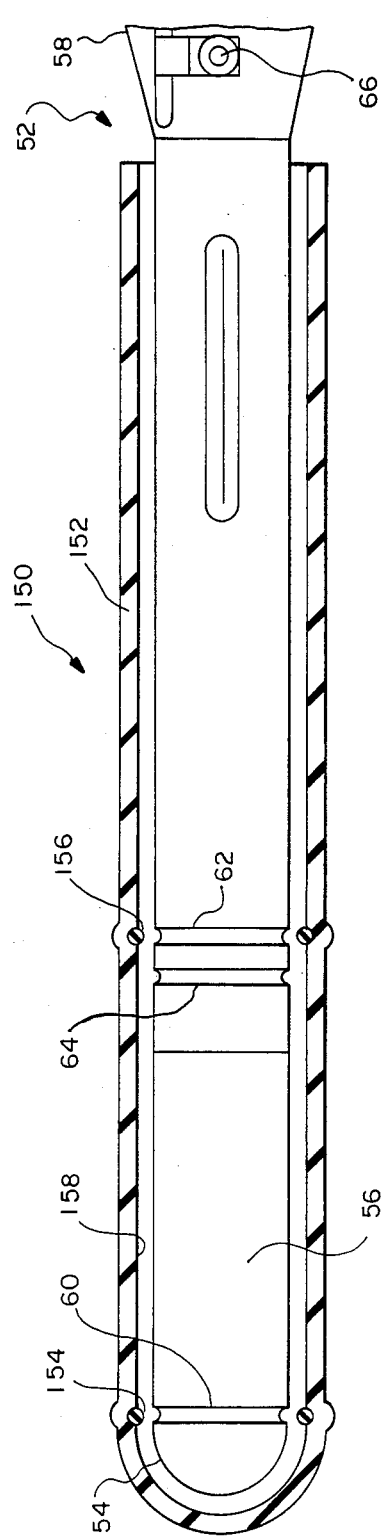

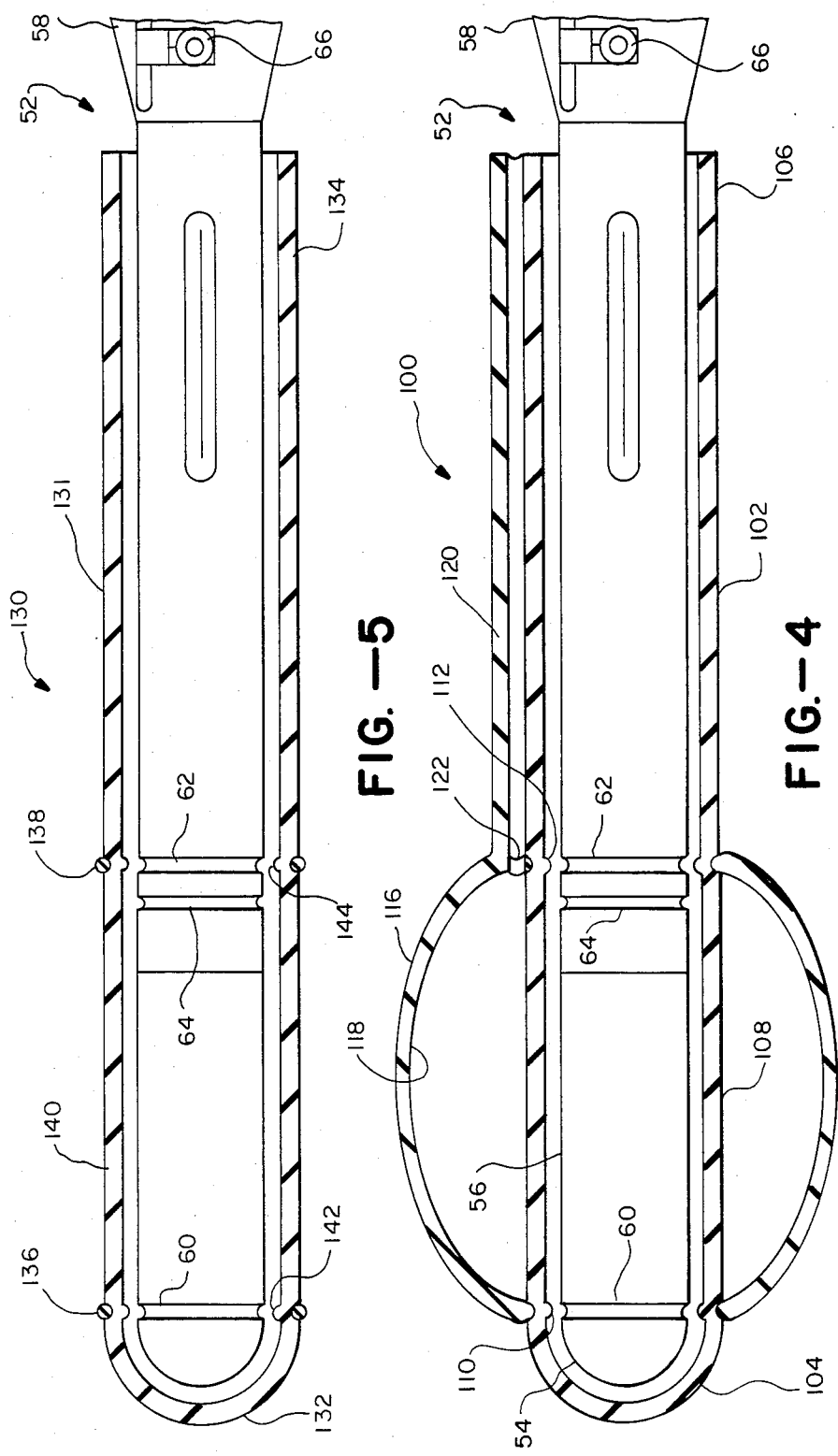

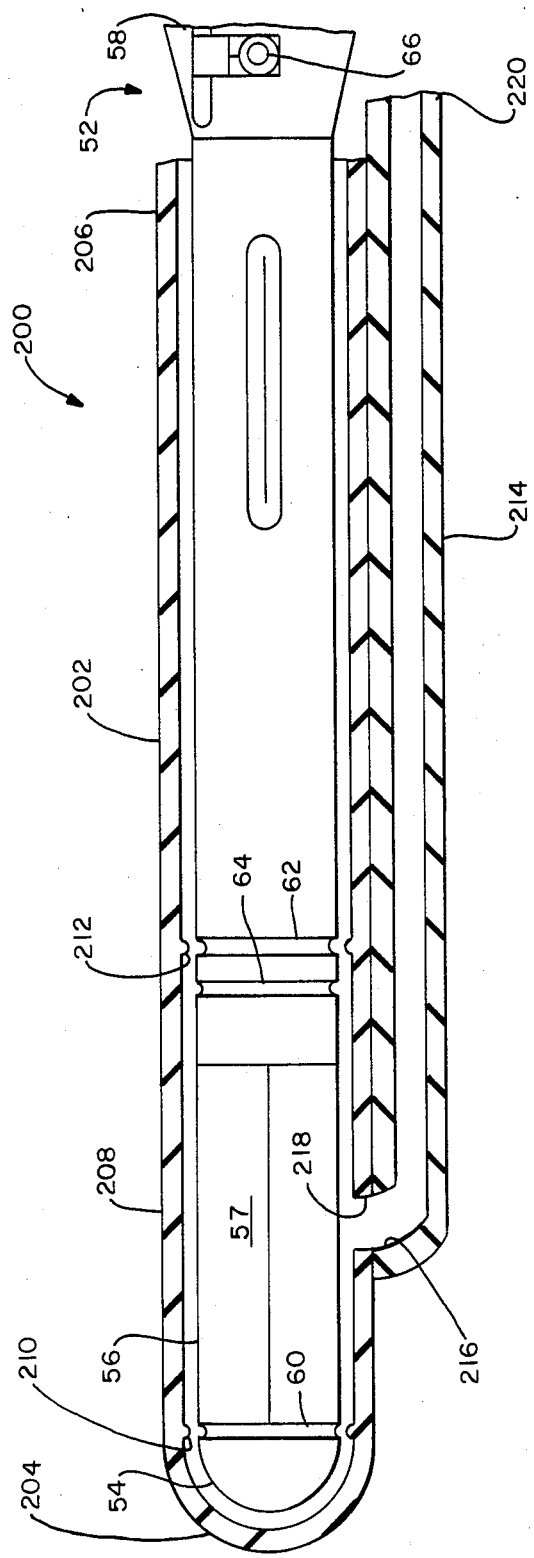
FIG.—7

4,815,470

INFLATABLE SHEATH FOR ULTRASOUND PROBE

FIELD OF THE INVENTION

The present invention relates to inflatable sheaths for ultrasound probes and in particular to sheaths which are inflatable with an ultrasound transmitting fluid so as to fill the space in a bodily cavity located between the ultrasound transducer of the probe and the cavity.

BACKGROUND OF THE INVENTION

The existing currently available sheaths for ultrasound probes generally include a cylindrical body which can be comprised of an ultrasound latex and which is designed to fit snugly about an ultrasound probe. The sheath is flexible such that on the application an ultrasound fluid under pressure the sheath will expand. Accompanying the sheath are generally one or two separate bands again comprised of ultrasound latex. An available ultrasound probe can include a first and a second sheath seal groove which are located on either side of a portion of the probe from which the ultrasound signals are transmitted and received. Located between the two grooves is a fluid outlet used for introducing fluid in order to cause the sheath to expand. As can be seen in FIG. 1, the probe is identified by the numeral 20 with the first and second sheath seal grooves by the numbers 22 and 24. The fluid outlet is identified by the number 26. The section containing the ultrasound transducer is identified by the number 28. A sheath 30 comprises a body 32 used in conjunction with the two bands 34 and 36. The bands 34 and 36 cause the sheath 30 to conform to the shape of and be received in the first and second sheath seal grooves 22 and 24 of the probe 20. Accordingly, fluid introduced through the outlet 26 can cause the portion of the sheath between the bands 32 and 34 to expand causing the sheath between said bands to conform to the shape of the bodily cavity into which the probe 20 and sheath 30 are inserted. Properly filled with appropriate ultrasound transmitting fluid, the sheath 30 thus causes the probe 20 to be stably positioned within the bodily cavities so that the probe will not move while an ultrasound image is being processed and additionally allows for a clear transmission and reception of the ultrasound signal from the probe 20 through the fluid contained by the sheath 30 to the bodily organ being examined.

In practice, there is a tendency for ultrasound fluid to escape past the first band 34 and into the area defined by the end of the sheath 38 and the end of the probe 40. This causes the end of the sheath 38 to expand. If this condition has occurred, with the subsequent removal of the probe from the bodily cavity after an examination is completed, there exists the possibility that the first band 34 can slip off of the sheath 30 and remain in the bodily cavity after the probe is fully removed therefrom.

Accordingly the present invention is directed to overcoming this disadvantage.

SUMMARY OF THE INVENTION

A sheath of the invention is provided for use with an ultrasound probe which probe has a front insertion end, a middle section containing an ultrasound transistor, and a handle end. The probe has a first sheath seal groove located between the front insertion end and the middle section and a second sheath seal groove located between the middle section and the handle end. The probe also has a fluid outlet located between the first and second sheath seal grooves. The sheath of the invention comprises an elongated cylindrical body having a first and a second end wherein the first end is closed and said second end is open and adapted to allow for the reception of the ultrasound probe. The sheath is adapted to cover at least the front insertion end, the first sheath seal groove, the middle section, the fluid outlet, the second sheath seal groove and to extend toward the handle end. The sheath is flexible and has an end cap which is formed about the first insertion end and extends toward the first sheath seal groove. Said end cap is of a thickness greater than the thickness of the cylindrical body so that said end cap is substantially less flexible than the body. Further means are provided for at least partially conforming the sheath body to the second sheath seal groove.

In another aspect of the invention, a band is provided for partially conforming the sheath body to the first sheath seal groove.

In another aspect of the invention, the sheath body of the sheath has substantially the same thickness as the end cap of the sheath.

In a further aspect of the invention the sheath body has sufficient flexibility in order to be able to expand when fluid is introduced between said sheath and the probe at the fluid outlet and said end cap in combination with said front insertion end is of sufficiently less flexibility such that said end cap does not expand with the portion of the sheath body located adjacent the middle portion of the probe.

In another asepct of the invention, the sheath body includes a first portion that is adapted to be inserted into the first sheath seal groove and a second portion adapted to be inserted into the second sheath seal groove.

Yet in another aspect of the invention the sheath includes a band adapted to cause a sheath body to be urged into the second sheath seal groove.

As a further aspect of the invention, the sheath includes a second cylindrical body means concentral with the first cylindrical body means and forming a chamber with the first cylindrical body. The chamber is adapted to be adjacent a middle section of a probe. The first cylindrical body and a second cylindrical body are both flexible. A conduit is provided integral with the first cylindrical body for introducing fluid into the chamber.

In another aspect of the invention the chamber is provided in the shape of a torus.

A further aspect of the invention includes a sheath and first and second bands which are integral with the body of the sheath and adapted for at least partially conforming the body of the sheath to the first and second sheath seal grooves.

In another aspect of the invention, the sheath includes first and second bands integral therewith which are adapted for being received by the first and second sheath seal grooves of a probe.

In another aspect of the invention, the sheath includes a tube provided externally thereto which communicates with the space between the sheath and the probe at a location opposite to where a transducer window is provided in the probe. Accordingly fluid can be introduced through the tube into the space between the sheath and the probe at the location of the ultrasound transducer without interfering with probe placement.

An object of the present invention is to provide a sheath which can be appropriately filled with ultrasound transmitting fluid in order to stabilize the probe inside a bodily cavity.

A further object is to provide for the transmission of an ultrasound signals between the probe and the tissue being examined with a minmum of interference with the signal.

Another object of the invention is to provide the ultrasound transmitting fluid adjacent to the ultrasound transducer of the probe and to contain the fluid immediately adjacent thereto.

Yet a further object of the invention is to provide for the elimination of ultrasound transmitting fluid from being received by the sheath other than where desired.

BRIEF DESCRIPTION OF THE FIGURES

FIG. 1 is a depiction of a prior art sheath positioned about an ultrasound probe.

FIG. 2 depicts a sectional view of a first embodiment in accordance with the present invention.

FIG. 3 depicts a sectional view of a variation of the embodiment of FIG. 2 of the present invention.

FIG. 4 depicts a sectional view of a second embodiment of the invention.

FIG. 5 depicts a sectional view of a third embodiment of the invention.

FIG. 6 depicts a sectional view of a variation of the embodiment of FIG. 5.

FIG. 7 depicts a sectional view of another embodiment of the invention.

DETAILED DESCRIPTION OF THE PREFERRED EMBODIMENT

With respect to the figures and in particular to FIG. 2, a first preferred embodiment of the sheath 50 of the invention is depicted in position around a probe 52. Probe 52 includes a front insertion end 54, a middle section 56 which houses the ultrasound transducer and a handle end 58. The probe 52 further includes first and second sheath seal grooves 60 and 62 which border on either side of the middle section 56. Between the grooves 60 and 62 and adjacent groove 62 is a fluid outlet 64 which has provided thereto fluid through a conduit internal to the probe 52 from a fluid inlet 66.

The sheath 50 of the inventon includes a first cylindrical body 70 which in the preferred embodiment is comprised of a latex material known in the industry for its ultrasound properties. The body has a closed end 72 and an open end 74. The open end receives the probe 52 such that the body 70 covers the front insertion end 54, the middle section 56, the grooves 60 and 62, the fluid outlet 64 and extends toward the handle end 58. In a preferred embodiment, a cap end 76 is formed integrally with the closed end 72 and extends in a hemispherical manner back and adjacent to the first sheath seal groove 60. In a preferred embodiment the end cap 76 is comprised of the same material as the body 70. The end cap 76 can be molded integrally and at the same time as the body 70. Alternatively, the body 70 can be formed first and then when the latex is in receptive state end 72 of the body 70 can be dipped into latex to form the cap end 76. In a preferred embodiment the cap end 76 has a thickness which is substantially about the same as the body 70, thus the combined thickness of the closed end 72 of body 70 and the cap end 76 is approximately double that of the rest of the body 70. Other variations are possible and fall within the scope of the invention.

It is also to be understood that the end cap 76 may extend over the closesd end 72 without the necessity of extending adjacent to the first groove 60.

A band 78 then can be provided which is independent from the body 70. Band means 78 is additionally made of an ultrasound latex and is elastic and flexible as is the body 70. Band 78 when fit about the body 70 urges the body 70 into the second groove 62. In a preferred embodiment an annular recess 80 is provided for receiving the band 78. Further the body 70 can include annular projection 82 and 84 which can be received by the first and second groove 60 and 62 respectively. It is to be understood that annular recess 80 and annular projections 82 and 84 are not required for the proper functioning of the sheath 50 of the invention, but enhance such functioning.

It is further to be understood that the body 70 is relatively flexible in comparison to the more rigid end cap 76 in combination with a closed end 72. Accordingly when fluid such as water is injected at inlet 64 the water is contained between groove 60 and 62 due to the urging by band 78 of the sheath 70 into groove 62 and due to the rigidity of the end cap 76. Accordingly a portion 86 of the body 70 which is located adjacent the middle section 56 is urged to balloon outwardly into the shape of a torus.

When the probe is inserted into a cavity and fluid under pressure is applied, the ballooning feature of the sheath 70 causes the portion 86 to conform to the walls of the cavity so as to immobilize and position the probe inside of the cavity. Further as the fluid in the preferred embodiment is water or other ultrasound receptive fluid, there is a continuum of signal from the probe through the fluid to the body organ being evaluated and back to the probe without discontinuities. Further it is to be understood that fluid does not cause the closed end 72 to balloon out due to the rigidity caused by the end cap 76. Removal of the probe 52 from the cavity is accomplished with the reduction of fluid pressure in the sheath 50 and the extraction of the probe 52 and the sheath 50 from the cavity.

It is to be understood that the present invention can be used in conjunction with a probe described and claimed in co-pending U.S. patent application entitled "Ultrasonic Probe" filed on Nov. 5, 1986 and given the U.S. Ser. No. 927,649, the contents of which are incorporated herein by reference.

An alternate of the embodiment of the invention which follows closely with the embodiment of FIG. 2 is shown in FIG. 3. In FIG. 3, like elements are numbered similarly to FIG. 2. In FIG. 3 a second band 90 similar to band 78 is positioned adjacent the end cap 76 and also adjacent the first groove 60. Band 90 performs the same function as does band 78. Further an annular recess 92 is formed in the body 70 to receive the band 90. Band 92 and the combination of the end cap 76 and the closed end 72 insure that closed end 72 does not balloon out when fluid is introduced between the probe and portion 86. Accordingly when the probe is removed and the fluid pressure is reduced, band 90 is not left in the cavity as has occurred with prior devices as previously discussed. It is to be understood that band 90 can be formed integrally with sheath 50 as taught by band 136 and sheath 130 in FIG. 5.

Another embodiment of the sheath 100 of the invention is depicted in FIG. 4. Sheath 100 includes a first cylindrical body 102 which has a closed end 104 and an open end 106.

The sheath 100 additionally includes a middle section 108 which is located adjacent to the middle section 56 of the probe 52. Sheath 100 can include internal annular projections 110 and 112. These projections 110, 112 may be received in the first and second groove 60 and 62 of probe 52 to properly register the sheath 100 relative to the probe 52. It is to be understood that the sheath 100 of the invention can function in accordance with the invention without the annular projections 110 and 112.

A second cylindrical body 116 is formed about and integral with the cylindrical body 102. In a preferred embodiment first and second cylindrical bodies 102 and 116 are of substantially the same thickness. The cylindrical body 116 is secured to the body 102 at positions adjacent the first and second grooves 60, 62 of the probe. Second cylindrical body 116 and the middle section 108 of the first cylindrical body 102 define therebetween a toroidal chamber 118. Further the sheath 100 includes a conduit 120 which extends along the cylindrical body 102 and external thereto and communicates with the toroidal chamber 118 through a port 122. Fluid under pressure can be inserted through conduit 120 so that it can expand the chamber 118. As with the prior embodiments, the sheath 100 of this embodiment is comprised of ultrasound latex. The latex is sufficiently flexible such that fluid under pressure can be used to balloon out the cylindrical body 116 once the probe is inserted into a cavity. The sheath 100 thus fixedly positions the probe in the cavity and allows for uninterrupted transittal and reception of ultrasound signals.

In order to remove the probe from the cavity, the toroidal chamber 118 is deflated with the removal of fluid and the sheath 100 is removed along with the probe. Unlike with the prior art, there is no possibility that elements of the sheath can be left in the cavity.

Another embodiment of the invention, sheath 130, is shown in FIG. 5. Sheath 130 includes a closed end 132 and an open end 134. Sheath 130 further includes first and second bands 136 and 138 which are integral with sheath body 131. Band can be individually formed and then secured to the body 131 as for example when the body 131 is not as yet fully cured. Bands 136 and 138 are flexible and elastic in order to urge the body 131 into the first and second grooves 60 and 62 of the probe 52. Bands 136 and 138 can comprise the same ultrasound material as the sheath 130. The middle portion 140 of the body 131 can expand with the introduction of fluid through port 64. Again annular projections 142 and 144 are depicted which are received in the grooves 60 and 62. As is to be understood, these projections are enhancements to the sheath 130, but not required for the proper function of the sheath.

An alternate version of the embodiment of FIG. 5 is shown in FIG. 6. This embodiment includes a sheath 150 with a body 152 which has integrally secured therewith bands 154 and 156 on the internal surface 158 of the body 152. The band members 154 and 156 in a preferred embodiment can be secured to and made integral with the body 152 while the body 152 is not finally cured. The bands 154 and 156 are adapted to be received in the grooves 60 and 62 in order to define a chamber between the integral surface 158 of the body 152 and the middle portion 56 of the probe. With the introduction of fluid into chamber 160, the probe 52 can be stabilized in the cavity and provide for transmittal of ultrasound signals to and from the probe 52.

Another embodiment of the sheath 200 of the invention is depicted in FIG. 7. Sheath 200 includes a first cylindrical body 202 which has a closed end 204 and an open end 206.

The sheath 200 additionally includes a middle section 208 which is located adjacent to the middle section 56 and window 57 of the probe 52. Through window 57 an ultrasound transducer sends and receives an ultrasound signal. Sheath 200 can include internal annular projections 210 and 212. These projections 210, 212 may be received in the first and second groove 60 and 62 of probe 52 to properly register and retain the sheath 200 relative to the probe 52. It is to be understood that as with all the above internal annular projections, projection 210 and 212 can include bands, such as for example latex bands, which are elastic and hold sheath 200 against probe 52 with the elastic nature of these projections retaining projections 210 and 212 in grooves 60, 62. Further it is to be understood that the sheath 200 of the invention can function in accordance with the invention without the annular projections 210 and 212. Also it is noted that the projections can be replaced by exterior bands, such as for example bands 78 and 90 in FIG. 3.

A tube 214 is positioned adjacent to and along the sheath 200. Tube 214 includes a first end 216 which communicates with a port 218 in the sheath 220. This port 218 and tube 214 are on the underside of the probe opposite the transducer window 57 so that the tube 214 does not interfere in any way with probe placement and imaging through window 57. The tube 214 includes a second end 220 which is located adjacent end 206 of the sheath 200. In a preferred embodiment, the tube 214 is substantially more rigid than the sheath 200 and can be comprised of what is generally known as surgical tubing. This tube 214 is secured to the sheath 200 as the sheath 200 is formed and before it it totally cured and dried. Thus the tube 214 becomes bonded to the sheath 200. In a preferred embodiment, the outer diameter of the tube 214 can be approximately ¼ of an inch with the thickness of the tube 214 being about 1/16 of an inch. Thus when the sheath 200 and tube 214 is inserted into a bodily cavity, it will not be pinched off by muscles such as for example the sphincter muscle. With the arrangement of a sheath 200, fluid can be introduced to the space between the sheath 200 and the probe 52 opposite the transducer window 57 so that fluid can fill the space between the projections 210 and 212 and between the middle portion 208 of the sheath 200 and the middle portion 56 of the probe 56.

INDUSTRIAL APPLICABILITY

In operation, the sheath of the embodiments of the invention are stretched over the probe 52 to form a snug fit about the probe. Fluid under pressure is then introduced so as to cause a chamber to be inflated, positioning the probe in the cavity and affording uninterrupted transfer of ultrasound signals. Once the diagnosis procedure is completed on a patient, fluid from the chamber is removed and the sheath and the probe are removed from the bodily cavity without leaving any portion of the sheath in the cavity as may happen with prior devices.

It is to be understood that other embodiments of the invention can be made and fall within the spirit and scope of the invention as described and claimed.

Other aspects and objects of the invention can be obtained from a review of the claims and the figures.

We claim:

1. A sheath for use with an ultrasound probe which has a front insertion end, a middle section containing an ultrasound transducer and a handle end, the middle section defining a front end located adjacent the front insertion end and a back end located adjacent the handle end, the transducer being located between the front and back ends, and a fluid outlet located adjacent the middle section, said sheath comprising:

an elongate cylindrical sheath body having a first end and a second end, and wherein said first end is closed and said sescond end is open and adapted to allow for the reception of an ultrasound probe such that said sheath is adapted to cover at least a front insertion end, the middle section, and a fluid outlet, and to extend toward the handle end of a probe;

said sheath body being flexible;

said sheath having an integral end cap formed about said first end and extending toward and adapted to end at a position adjacent about a front end of a middle section with a probe inserted into the sheath;

said end cap and said first end being substantially less flexible than said sheath body; and means adapted for at least partially conforming said sheath body to a probe at a position adjacent a back end of a middle section for defining a chamber between said end cap and said conforming means in order to accept and retain fluid adjacent a transducer.

2. The apparatus of claim 1 wherein the end cap has a thickness which is substantially the same as the thickness of the body.

3. The apparatus of claim 1 wherein:

said body has sufficient flexibility in order to be able to expand when fluid is introduced at the fluid outlet between said sheath and the probe and said end cap in combination with said first end is sufficiently less flexible such that said end cap does not expand.

4. The apparatus of claim 1 wherein said partially conforming means is integral with the body.

5. The apparatus of claim 1 wherein the probe further has a first sheath seal groove located between the front insertion end and the middle section and a second sheath seal groove located between the middle section and the handle end, wherein:

said sheath body includes an annular projection adapted to be inserted into the second sheath seal groove.

6. The apparatus of claim 5 wherein:

said body includes another annular projection adapted to be inserted into the first sheath seal groove.

7. The apparatus of claim 5 including:

second means adapted for at least partially conforming said body to the first sheath seal groove.

8. A sheath for use with an ultrasound probe which has a front insertion end, a middle section containing an ultrasound transducer and a handle end, and first and second sheath seal grooves, the first sheath seal groove located between the front insertion end and the middle section and the second sheath seal groove located between the middle section and the handle end, said sheath comprising:

a first elongate cylindrical body having a first end and a second end, and wherein said first end is closed and said second end is open and adapted to allow for the reception of an ultrasound probe such that said sheath is adapted to cover at least a front insertion end, middle section, and to extend toward a handle end of a probe;

a second cylindrical body means integral with the first cylindrical body for forming a chamber with the first cylindrical body, which chamber is adapted to be adjacent a middle section of a probe;

said first cylindrical body and said second cylindrical body means being flexible;

a first annular projection adapted to be received in a first sheath seal groove;

a second annular projection adapted to be received in a second sheath seal groove.

means integral with the first cylindrical body for introducing fluid into said chamber.

9. The apparatus of claim 8 wherein:

the fluid introducing means includes a conduit integral with the portion of the first cylindrical body adapted to extend from the middle section of a probe rearwardly toward a handle end.

10. The apparatus of claim 8 wherein said chamber has a toroidal shape.

11. The apparatus of claim 8 wherein:

said first cylindrical body has a first thickness and said second cylindrical body means has a second thickness, said first and second thickness being substantially similar.

12. A sheath for use with an ultrasound probe which has a front insertion end, a middle section containing an ultrasound transducer and a handle end, which probe further has a first sheath seal groove located between the front insertion end and the middle section and a second sheath seal groove located between the middle section and the handle end and a fluid outlet located between the first and second sheath seal grooves, said sheath comprising:

an elongate cylindrical sheath body having a first end and a second end, and wherein said first end is closed and said second end is open and adapted to allow for the reception of the ultrasound probe such that said sheath is adapted to cover at least the front insertion end, middle section, the first and second sheath seal grooves and the fluid outlet, and to extend toward the handle end;

first means integral with the sheath body adapted for at least partially conforming said body to the first sheath seal groove;

second means integral with the sheath body adapted for at least partially conforming said body to the second sheath seal groove; and said sheath body has sufficient flexibility in order to be able to expand when fluid is introduced between said sheath and the probe at the fluid outlet.

13. The apparatus of claim 12 wherein:

said first and second means are externally to said sheath body such that said body is adapted to be located between the probe and the first and second means, such that the first and second means urge said body into the first and second sheath seal grooves respectively.

14. The apparatus of claim 13 wherein:

said body includes a first and second annular projection adapted for being received in the first and second sheath seal grooves respectively.

15. The apparatus of claim 12 wherein:

said first and second means are internal to said sheath body and said first and second means are adapted to at least partially fit into said first and second sheath seal grooves.

16. A shseath for use with a probe which has a front insertion end, a middle section containing a transducer and a handle end, the middle section defining a front end located adjacent the front insertion end and a back end located adjacent the handle end, the transducer being located between the front and back ends, and a fluid outlet located adjacent the middle section, said sheath comprising:

an elongate cylindrical sheath body having a first end and a second end, and wherein said first end is closed and said second end is open and adapted to allow for the reception of a probe such that said sheath is adapted to cover at least a front insertion end, a middle section, and a fluid outlet, and to extend toward a handle end of a probe;

said sheath body being flexible;

said sheath having an integral end cap formed about said first end and extending toward and adapted to end at a position adjacent about a front end of a middle section with a probe inserted into the sheath;

said end cap and said first end being substantially less flexible than said sheath body; and means adapted for at least partially conforming said sheath body to the probe at a position adjacent a back end of a middle section for defining a chamber between said end cap and said conforming means in order to accept and retain fluid adjacent a transducer.

17. A sheath for use with a probe which has a front insertion end, a middle section containing a transducer and a handle end, and first and second sheath seal grooves, the first sheath seal groove located between the front insertion end and the middle section and the second sheath seal groove located between the middle section and the handle end, said sheath comprising:

a first elongate cylindrical body having a first end and a second end, and wherein said first end is closed and said second end is open and adapted to allow for the reception of a probe such that said sheath is adapted to cover at least a front insertion end, middle section, and to extend toward a handle end of a probe;

a second cylindrical body means integral with the first cylindrical body for forming a chamber with the first cylindrical body, which chamber is adapted to be adjacent a middle section of a probe;

said first cylindrical body and said second cylindrical body means being flexible;

a first annular projection adapted to be received in a first sheath seal groove, and a second annular projection adapted to be received in a second sheath seal groove.

means integral with the first cylindrical body for introducing fluid into said chamber.

18. A sheath for use with an ultrasound probe which has a front insertion end, a middle section containing an ultrasound transducer and a handle end, and first and second sheath seal grooves, the first sheath seal groove located between the front insertion end and the middle section and the second sheath seal groove located between the middle sheath and the handle end, said sheath comprising:

an elongate cylindrical body having a first end and a second end, and wherein said first end is closed and said second end is open and adapted to allow for the reception of an ultrasound probe such that said sheath is adapted to cover at least the front insertion end, middle section, and to extend toward the handle end;

a first annular projection adapted to be received in the first sheath seal groove; and a second annular projection adapted to be received in the second sheath seal groove;

a tube positioned external and adjacent to the first cylindrical body;

said cylindrical body having a port therethrough which is adapted to be positioned at about the location of a middle section of a probe with the sheath receiving a probe;

said tube having a first end which communicates with said port and a second end which is adjacent said second end of said cylindrical body.

said first cylindrical body being more flexible than said tube.

19. The apparatus of claim 18 wherein said tube is integral with said cylindrical body.

20. The apparatus of claim 13 wherein the middle section of the probe includes a transducer window which is transparent to ultrasound signals and wherein:

said port in said sheath is adapted to be located away from the transducer window so that said tube does not interfere with the placement of the transducer window adjacent an object which is to be probed with an ultrasound signal.

* * * * *